US006211296B1

(12) United States Patent
Frate et al.

(10) Patent No.: US 6,211,296 B1
(45) Date of Patent: Apr. 3, 2001

(54) HYDROGELS CONTAINING SUBSTANCES

(75) Inventors: Dean M. Frate, Cleveland; Joseph A. Chiarelli, Broadview Heights, both of OH (US); Yong Ma, Beverly Hills, CA (US)

(73) Assignee: The B. F. Goodrich Company, Brecksville, OH (US)

( * ) Notice: Subject to any disclaimer, the term of this patent is extended or adjusted under 35 U.S.C. 154(b) by 0 days.

(21) Appl. No.: 09/430,044

(22) Filed: Oct. 29, 1999

Related U.S. Application Data
(60) Provisional application No. 60/107,237, filed on Nov. 5, 1998.

(51) Int. Cl.$^7$ ............................. C08L 33/02; C08L 33/08; C08L 33/10; C08L 35/00
(52) U.S. Cl. ......................... 525/207; 524/517; 524/556
(58) Field of Search ................................. 525/207, 201; 524/517, 522, 556

(56) References Cited

U.S. PATENT DOCUMENTS

| 2,798,053 | 7/1957 | Brown . | |
|---|---|---|---|
| 2,923,692 | 2/1960 | Ackerman et al. . | |
| 3,915,921 | 10/1975 | Schlatzer, Jr. . | |
| 4,258,104 | * 3/1981 | Lee et al. | 428/342 |
| 4,375,533 | 3/1983 | Park et al. . | |
| 4,419,502 | 12/1983 | Sehm . | |
| 4,492,724 | * 1/1985 | Allbright et al. | 428/40.9 |
| 4,585,820 | * 4/1986 | Defago et al. | 524/232 |
| 4,639,490 | 1/1987 | Masler, III et al. . | |
| 4,971,790 | 11/1990 | Magruder et al. . | |
| 5,079,034 | * 1/1992 | Miyake et al. | 427/521 |
| 5,219,916 | * 6/1993 | Den Hartog et al. | 524/515 |
| 5,288,814 | 2/1994 | Long, II et al. . | |
| 5,349,030 | 9/1994 | Long, II et al. . | |
| 5,373,044 | 12/1994 | Adams et al. . | |
| 5,468,797 | 11/1995 | Adams et al. . | |
| 5,478,568 | 12/1995 | Takayasu et al. . | |
| 5,496,819 | 3/1996 | Okuyama et al. . | |
| 5,525,356 | 6/1996 | Jevne et al. . | |
| 5,607,690 | 3/1997 | Akazawa . | |
| 5,656,646 | * 8/1997 | Perner et al. | 510/361 |
| 5,753,742 | * 5/1998 | Bumanlag | 524/501 |
| 5,962,571 | * 10/1999 | Overbeek et al. | 524/460 |

FOREIGN PATENT DOCUMENTS

| 736022 | * 6/1966 | (CA) . |
| 0 177 805 | 4/1986 | (EP) . |
| 0 436 217 A2 | 7/1991 | (EP) . |

OTHER PUBLICATIONS

Patent Abstracts of Japan, vol. 1997, No. 07, Jul. 31, 1997 & JP 09 087172 A (Lion Corp), Mar. 31, 1997 abstract.

* cited by examiner

Primary Examiner—Vasu Jagannathan
Assistant Examiner—Callie E. Shosho
(74) Attorney, Agent, or Firm—Brian M. Kolkowski; Daniel J. Hudak

(57) ABSTRACT

A blend of one or more crosslinked polymers or copolymers prepared from an olefinically unsaturated polymerizable carboxylic or anhydride monomer and at least one high molecular weight essentially linear polymer prepared from an olefinically unsaturated polymerizable carboxylic acid monomer. The blend is neutralized to typically a low pH, and generally contains a noncovalent, e.g. ionic, crosslinking agent, and a cure rate modifier. The hydrogel blend is capable of containing a large amount of water, has good tack, good adhesion, and can be utilized as an application vehicle having a backing thereon as well as containing various substances such as personal care compounds, pharmaceuticals, active ingredients, and the like.

20 Claims, No Drawings

HYDROGELS CONTAINING SUBSTANCES

CROSS REFERENCE

This patent application is based upon U.S. Provisional Application Ser. No. 60/107,237, filed Nov. 5, 1998.

BACKGROUND OF THE INVENTION

1. FIELD OF THE INVENTION

The present invention relates to articles created using blends of polymers and other ingredients, and to a process for preparing the same. The articles serve as a hydrogel for applying various substances to a substrate. The substance can be a personal care compound, a biologically active compound, an active ingredient, an absorptive material, etc. The substrates can be living organisms, or inanimate objects.

2. BACKGROUND ART

The earliest cataplasms were probably called poultices. A poultice is a medicated mass (often clay, herbal component, and a carrier such as water) spread on cloth and applied to the skin, often for sores or other lesions. Later, various gels and viscosity modifiers were added to cataplasms. Typically and preferably, a cataplasm has direct contact with skin or the substrate to be treated. As prepared commercially in a multiple cataplasm package, a cataplasm often has a backing on one side, which provides physical strength and a durable exposed surface during use on the substrate, and a release layer on the other side, which is removed before application to the substrate.

Transdermal delivery systems have been developed for various pharmaceutical applications. They generally transfer a medicine through the skin rather than to the skin. The active ingredients in commercial transdermal delivery systems are usually limited to a single chemical compound or a family of compounds. These systems are typically more expensive than oral medication and comprise an impermeable backing layer, a reservoir, a metering layer, and an adhesive layer. The system is usually protected by a release layer.

SUMMARY OF INVENTION

Hydrogels containing various substances or compounds such as personal care compounds, pharmaceuticals, etc., are described. The hydrogel contains significant amounts of water therein and is a blend of a crosslinked polymer and a high molecular weight essentially linear polymer. Noncovalent crosslinks, such as ionic crosslinks in the presence of cure rate modifiers, permit the hydrogel to be formed into a suitable end product before being cured.

DETAILED DESCRIPTION OF THE INVENTION

From a compositional aspect, the hydrogel is a blend of at least two polymers one of which is a crosslinked polymer derived from one or more olefinically unsaturated polymerizable carboxylic monomers and optionally one or more comonomers. The other polymer is a high molecular weight substantially linear polymer derived from one or more olefinically unsaturated polymerizable carboxylic acid monomers. The hydrogel also contains a neutralizing agent; desirably a noncovalent crosslinking agent; and a cure rate modifier; and is generally located on a backing with a release compound or liner covering the hydrogel. The hydrogel is typically applied to a substrate such as human skin and contains therein a substance such as a personal care compound, a pharmaceutical, an active ingredient, or the like; The hydrogel is typically located on a substrate.

In some embodiments, the hydrogel removes a compound from the substrate by binding an absorptive substance to the substrate. That is, the hydrogel and its active ingredient act as absorbents of an impurity or irritants. An example of this would be the removal of undesired oil or other components from the skin. The hydrogel offers a new way to deliver or remove some compounds (those not before applied with cataplasms) to/from various substrates with improved performance attributes.

The hydrogel comprises any natural or synthetic polymer that is highly swollen by water. In the cataplasm application the hydrogel and its backing desirably remain a coherent mass, i.e. it doesn't fracture during application, removal, or use and can be discarded as a single unit of waste. It is generally desired that none of the hydrogel, other than the delivered substance, remain on the substrate after use. The backing can be any material convenient to the particular application. It is generally only present for ease of handling and integrity purposes, although it can facilitate application and solvent retention. Wovens, nonwovens, and films such as plastic can be used as backings. Natural or synthetic products can also be used. The release liner can be any suitable material known to the art or to the literature and generally is a plastic which optionally contains a release agent thereon such as a silicone.

Desirably the hydrogel is crosslinked or otherwise linked together as an integral material (e.g. a polymer and/or a noncontinuous hydrogel can be connected together via interentanglement of the chains, crystalline crosslinks, ionic crosslinks, hydrogen bonds, etc). For the purposes of this specification, integral will mean some connection, either temporary or permanent, that allows the hydrogel to function as a solid at typical storage and use temperatures of the particular substance. Function will imply that the hydrogel does not unduly flow, fracture, or fragment during use, but understandably does not imply tremendous physical integrity, which is not generally required. The preferred polymers forming the hydrogel will be gel-like particles that have the capacity to increase their volume by swelling in water by a factor from about 10 to about 1000 or 10,000. Preferably, they swell from about 10, 20, 30, or 40 times to about 500 or 1000 times their original volume.

Polyurethanes may also be used in the hydrogel. These may be thermoplastic or elastomeric polyurethanes. They may be hydrophobic, hydrophilic or amphiphilic depending on the active ingredients or other additives to be incorporated into the hydrogel. Polyurethanes and their precursor are well known to the art. It is preferred that the polyurethanes only be an additive to the hydrogel and that they be appropriately functionalized or processed to be uniformly dispersed in the hydrogel.

According to the present invention, an olefinically unsaturated polymerizable carboxylic monomer is utilized. Such monomers are described in detail and set forth in U.S. Pat. No. 5,468,797, as well as prior U.S. Pat. Nos. 5,373,044, and 5,288,814 thereof, which are hereby fully incorporated by reference with regard to all aspects thereof. As set forth in the '797 patent, the monomer contains at least one activated C=C group as well as a carboxyl or anhyride group. Such polymers can be homopolymers of an unsaturated, polymerizable carboxylic monomer containing from 3 to 34 carbon atoms, and preferably from 3 to 6 carbon atoms such as an acrylic acid, methacrylic acid, maleic acid, itaconic acid, maleic anhydride, and the like. The carboxyl containing polymers, before crosslinking, have molecular weights greater than about 500 to as high as several million, usually greater than about 10,000 to 900,000 or more.

Copolymers of the polymerizable carboxylic monomers can be made utilizing monomers having a total of from 3 to about 40 and desirably from 3 to about 34 carbon atoms such as acrylate esters, acrylamides, olefins, vinyl esters, vinyl ethers, vinyl amides, amines or styrenics. The amount of repeat units derived from such comonomers is generally from about 0.001 to about 30 percent and desirably from about 0.01 to about 20 percent by weight of the copolymer.

Typical materials are those described in U.S. Pat. No. 2,798,053. Copolymers, for example, include copolymers of acrylic acid with small amounts of polyalkenyl polyether cross-linkers that are gel-like polymers, which, especially in the form of their salts, absorb large quantities of water or solvents with subsequent substantial increase in volume. Other useful carboxyl containing polymers are described in U.S. Pat. No. 3,940,351, directed to polymers of unsaturated carboxylic acid and at least one alkyl acrylic or methacrylic ester where the alkyl group contains 10 to 30 carbon atoms, and U.S. Pat. Nos. 5,034,486; 5,034,487; and 5,034,488; which are directed to maleic anhydride copolymers with vinyl ethers. Other types of such copolymers are described in U.S. Pat. No. 4,062,817 wherein the polymers described in U.S. Pat. No. 3,940,351 contain additionally another alkyl acrylic or methacrylic ester and the alkyl groups contain 1 to 8 carbon atoms. Carboxylic polymers and copolymers such as those of acrylic acid and methacrylic acid also may be crosslinked with polyfunctional materials as divinyl benzene, unsaturated diesters and the like, as is disclosed in U.S. Pat. Nos. 2,340,110; 2,340,111; and 2,533,635. The disclosures of all of these U.S. patents are hereby incorporated herein by reference.

The carboxylic monomers are the olefinically-unsaturated carboxylic acids containing at least one activated carbon-to-carbon olefinic double bond, and at least one carboxyl group; that is, an acid or function readily converted to an acid containing an olefinic double bond which readily functions in polymerization because of its presence in the monomer molecule, either in the alpha or beta position with respect to a carboxyl group, —C=C—COOH; or as part of a terminal methylene grouping, CH2=C<. Olefinically-unsaturated acids of this class include such materials as the acrylic acids typified by acrylic acid itself, methacrylic acid, alpha-cyano acrylic acid, beta methylacrylic acid (crotonic acid), alpha-phenyl acrylic acid, beta-acryloxy propionic acid, cinnamic acid, p-chloro cinnamic acid, 5-phenyl-2,4-pentadienoic acid, itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same carboxylic acid molecule. Maleic anhydride and other acid anhydrides useful herein have the general structure

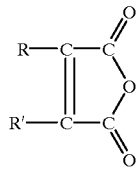

wherein R and R' are selected from the group consisting of hydrogen, halogen and cyanogen (—C≡N) groups and alkyl, aryl, alkaryl, aralkyl, and cycloalkyl groups such as methyl, ethyl, propyl, octyl, decyl, phenyl, tolyl, xylyl, benzyl, cyclohexyl, and the like.

The preferred carboxylic monomers are the monoolefinic acrylic acids having the general structure

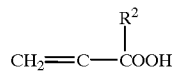

wherein $R^2$ is a substituent of hydrogen, halogen, and the cyanogen (—C≡N) groups, monovalent alkyl radicals, monovalent aryl radicals, monovalent aralkyl radicals, monovalent alkaryl radicals, and monovalent cycloaliphatic radicals. Of this class, acrylic and methacrylic acid are most preferred. Other useful carboxylic monomers are maleic acid and its anhydride.

The above noted polymers can be crosslinked with any polyene, e.g. decadiene or trivinyl cyclohexane; acrylamides, such as methylene bis acrylamide; polyfunctional acrylates, such as trimethylol propane triacrylate; or polyfunctional vinylidene monomer containing at least 2 terminal $CH_2$< groups, including for example, butadiene, isoprene, divnyl benzene, divinyl naphthalene, allyl acrylates and the like. Particularly useful crosslinking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2$=C<. They are made by the etherification of a polyhydric alcohol containing at least 2 carbon atoms and at least 2 hydroxyl groups. It is preferred to utilize polyethers containing an average of two or more alkenyl ether groupings per molecule. Other crosslinking monomers include for example, diallyl esters, dimethallyl ethers, allyl or methallyl acrylates and acrylamides, tetraaliyl tin, tetravinyl silane, polyalkenyl methanes, diacrylates, and dimethacrylates, divinyl compounds such as divinyl benzene, polyallyl phosphate, diallyloxy compounds and phosphite esters and the like. Also, polyallyl esters of poly(methacrylic acid) can be utilized. Typical agents are allyl pentaerythritol, allyl sucrose, trimethylolpropane triacrylate, 1,6-hexanediol diacrylate, trimethylolpropane diallyl ether, pentaerythritol triacryiate, tetramethylene dimethacrylate, ethylene diacrylate, ethylene dimethacrylate, triethylene glycol dimethacrylate, and the like. When the crosslinking agent is present, the polymeric mixtures usually contain up to about 5% or more by weight of crosslinking monomer based on the total of carboxylic acid monomer, plus other monomers, if present, and more preferably from about 0.01 to 3.0 weight percent by weight.

Preferred crosslinking agents include allyl pentaerythritol, trimethylolpropane diallylether, and ally sucrose.

In addition to the above described polymers and copolymers, an interpolymer of the same, can also be utilized. Such interpolymers are made by preparation of the above polymers or copolymers in the presence of a steric stabilizer surfactant. The steric stabilizer surfactant has at least one hydrophilic moiety and at least one hydrophobic moiety in a linear block or a random comb configuration, or mixtures thereof. The interpolymer can be mixed with a wetting additive such as a low surface tension surfactant, a glycol, a polyhydric alcohol, or mixtures thereof.

A detailed description of the preparation of the interpolymers, the steric stabilizer surfactants, the wetting additive, and the like is described in detail in U.S. Pat. No. 5,468,797 and accordingly is fully incorporated by reference. When the steric stabilizer is a linear block copolymer steric stabilizer, it is defined by the following formula:

$$C_w-(B-A-B_y-)_x-D_z,$$

where
- A is a hydrophilic moiety, having a solubility in water at 25° C. of 1% or greater, a molecular weight of from about 200 to about 50,000, and selected to be covalently bonded to the B blocks;
- B is a hydrophobic moiety, having a molecular weight of from about 300 to about 60,000, a solubility of less than 1% in water at 25° C., capable of being covalently bonded to the A blocks;
- C and D are terminating groups which can be A or B; can be the same or different groups, and will depend upon the manufacturing process, since they are present to control the polymer length, to add other functionality;
- w is 0 or 1;
- x is an integer of 1 or more;
- y is 0 or 1; and
- z is 0 or 1.

Examples of hydrophilic groups are polyethylene oxide, poly(1,3-dioxolane), copolymers of polyethylene oxide or poly(1,3-dioxolane), poly(2-methyl-2-oxazoline polyglycidyl trimethyl ammonium chloride, polymethylene oxide, and the like, with polyethylene oxide being preferred. Examples of hydrophobic groups are polyesters, such as those derived from 2-hydroxybutyric acid, 3-hydroxybutyric acid, 4-hydroxybutyric acid, 2-hydroxycaproic acid, 10-hydroxydecanoic acid, 12-hydroxydodecanoic acid, 16-hydroxyhexadecanoic acid, 2-hydroxyisobutyric acid, 2-(4-hydroxystearic propionic acid, 4-hydroxyphenylpyruvic acid, 12-hydroxystearic acid, 2-hydroxyvaleric acid, polylactones such as caprolactone or butyrolactone, polylactams such as those derived from caprolactam, polyurethanes, or polyisobutylene, where the hydrophobe should provide a steric barrier of greater than 50 Angstroms, preferably greater than 75 Angstroms, with greater than 100 Angstroms being also preferred, and the like, with polyhydroxy fatty acids, such as poly(12-hydroxystearic acid) being preferred. The steric barrier is the length of the hydrophobe in its fully extended condition. Such steric stabilizers are commercially available under the brand name Hypermer® from Imperial Chemicals Industries, Inc.

Steric stabilizer molecules comprise both hydrophilic and hydrophobic units. Hydrophobic polymer units or hydrophobic blocks may be prepared by a number of well known methods. These methods include condensation reactions of hydroxy acids, condensation of polyols (preferably diols) with polycarboxylic acids (preferably diacids). Other useful methods include polymerization of lactones and lactams, and the reactions of polyols with polyisocyanates. Polyisobutylenes can be prepared by acidic condensation of isobutene. Hydrophobic blocks or polymer units can be reacted with hydrophilic units by such reactions as are known to those skilled in the art. These reactions include condensation reactions and coupling reactions, for example. Subsequent to the steric stabilizer preparation, the stabilizers may be further reacted with modifying agents to enhance their utility. U.S. Pat. No. 4,203,877 to Alan S. Baker teaches making such steric stabilizers, and the entire disclosure thereof is incorporated herein by reference.

When the steric stabilizer is a random copolymeric comb steric stabilizer, it is defined by the following formula:

$$R_1-(Z)_m-(Q)_n-R_2,$$

where
- $R_1$ and $R_2$ are terminating groups and may be the same or different and will be different from Z and Q.
- Z is a hydrophobic moiety having a solubility of less than 1% in water at 25° C.,
- Q is a hydrophilic moiety, having a solubility of more than 1% in water at 25° C.,
- m and n are integers of 1 or more, and are selected such that the molecular weight of the polymer is from about 100 to about 250,000.

Examples of the hydrophobic monomer unit or moiety are dimethyl siloxane, diphenyl siloxane, methylphenyl siloxane, alkyl acrylate, alkyl methacrylate, and the like, with dimethyl siloxane being preferred.

Examples of the hydrophilic monomer unit or moiety are methyl-3-polyethoxypropyl siloxane-Ω-phosphate or sulfate, and the alkali metal or ammonium salts derived therefrom; units derived from polyethoxy (meth)acrylate containing from 1 to 40 moles of ethylene oxide; acrylic acid; acrylamide; methacrylic acid, maleic anhydride; dimethyl amino ethyl (meth)acrylate; or its reaction product with methyl chloride or dimethyl sulfate; dimethyl amino propyl(meth)acrylamide and its reaction product with methyl chloride or dimethyl sulfate, and the like, with methyl-3-polyethoxypropyl siloxane-Ω-phosphate being preferred.

Examples of terminating agents are monohalo silanes, mercaptans, haloalkanes, alkyl aromatics, alcohols, and the like, which will produce terminating groups such as trialkyl silyl, alkyl, aryl alkyl, alcoholate, and the like, with preferred terminating groups being trimethyl silyl.

The wetting additive is preferably a low surface tension surfactant (or wetting agent) and can be a fluorine containing, silicone containing or hydrocarbon surfactant, as long as it has an ability to reduce the surface tension of water (which is 72 dynes per centimeter at 25° C.), preferably to less than 40 dynes/cm at 25° C., with less than 30 dynes/cm being further preferred. By the term hydrocarbon surfactant we mean any surfactant which contains carbon, hydrogen, and oxygen and does not contain fluorine or silicon atoms. The amount of low surface tension surfactant will usually be less than 10% by weight based upon the weight of the acrylic acid interpolymer (10 phr), although 0.001 phr to 5.0 phr is preferred. The exact amount will depend upon the surfactant which is selected and its ability to reduce the surface tension of water. Those surfactants which can be used at the least dosage, such as a fluorine containing surfactant are preferred. Further, it was unexpectedly discovered that some of the surfactants are quite effective at very low dosages, such that the surfactant has no or little effect on the properties of the interpolymer in its use as a thickener, emulsifier, or thickening aid. Although not fully understood, it is believed that some of the surfactants when used in greater doses will result in increased wetting times because the additional surfactant will provide an additional coating on the polymer particles and slow the wetting process.

Table I shows a list of low surface tension surfactants which can be used in accordance with the present invention. The surface tension values represent the ability of a 1% by weight dosage of these surfactant to reduce the surface tension of water at 25° C. As can be appreciated, this list is considered representative and other low surface tension surfactants could be employed.

The surfactant employed can be anionic, cationic, or nonionic with nonionic surfactants being preferred. When the surfactants is added pre-polymerization, the cationic and anionic nature of the surfactant can play a part in or influence the polymerization, while the nonionic surfactants remain relatively inactive.

| SURFACTANT (*) (Trade Name) | SUPPLIER | COMPOSITION | SURFACE TENSION (Dynes/cm) 1% Dose @ 25° C. |
| --- | --- | --- | --- |
| Fluowet OTN (F/N) | Hoechst Celanese | Fluoroaliphatic ethoxylate | 18.09 |
| Forafac 1157N (F/N) | Atochem | Polyfluoralkyl betaine | 18.44 |
| Fluorad FC-170C (F/N) | 3M | Fluorinated alkyl polyoxyethylene ethanols | 19.95 |
| Florafac 1033 (F/N) | Atochem | Anionic fluorinated surfactant | 20.84 |
| Fluorad FC-171 (F/N) | 3M | Fluorinated alkyl alkoxlate | 20.84 |
| Silwet L-77 (S/N) | Union Carbide | Polyalkylenoxide-modified heptamethyl trisiloxane | 21.35 |
| Flourad FC-120 (F/A) | 3M | Ammonium perfluoroalkyl sulfonate | 21.17 |
| Zonyl FSP (F/A) | DuPont | Ammoniated phosphate fluorochemical | 23.04 |
| Zonyl FSN (F/N) | DuPont | Hydroxy terminated fluorochemical | 22.18 |
| Silwet L-7600 (S/N) | Union Carbide | Polyalkyleneoxide-modified polydimethyl siloxane | 24.88 |
| Silwet L-7602 (S/N) | Union Carbide | Polyalkyleneoxide-modified polydimethyl siloxane | 25.15 |
| Silwet L-7604 (S/N) | Union Carbide | Polyalkyleneoxide-modified polydimethyl siloxane | 24.30 |
| Dow Corning 193 (S/N) | Dow Corning | Silicone glycol copolymer | 28.93 |
| Neodol 25-7 (H/N) | Shell | $C_{12}$–$C_{15}$ linear primary alcohol ethoxylate | 28.84 |
| Glucopon 225CS (H/N) | Henkel | $C_8$–$C_{10}$ alkyl polysaccharide ether | 29.11 |
| Pecosil DIP 100 (H/N) | Phoenix Chemical | Dimethicone copolyol phosphate | 27.65 |
| Pecosil PS-100 (H/N) | Phoenix Chemical | Dimethicone copolyol phosphate | 30.35 |
| Pecosil PS-100-OP (H/N) | Phoenix Chemical | Dimethicone copolyol phosphate | 30.54 |
| Adogen 432 (H/C) | Ashland Chemical | Trialkyl ($C_8$–$C_{10}$) ammonium chloride | 30.21 |
| Triton X-100 (H/N) | Union Carbide | Polyoxyethylene ether | 31.32 |
| Alpha-Step MC-48 (H/A) | Stepan Company | α sulfomethyl ester | 33.54 |

(*) F = Fluorine containing; S = Silicone Containing; H = Hydrocarbon; A = Anionic; C = Cationic; N = Nonionic The wetting additive can be added to the monomers in polymerizing the polycarboxylic acid interpolymer or after polymerization, or in the case of the low surface tension surfactants, it also can be added to the water into which the interpolymer is to be dispersed. It is preferred that the wetting additive be admixed after or post-polymerization. It is theorized that, when the surfactant is added during polymerization, it remains with the polymer as an admixture, but a portion of the surfactant is trapped in the interstices of the interpolymer, so the same amount added pre-polymerization will not be as effective as that amount added post-polymerization of the interpolymer. Further, there is nothing critical in the method of addition. For example, the surfactant can be added as a liquid to the interpolymer while it is still in the polymerization solvent and before drying or it can be sprayed on the dry polymer powder which can then be subject to further drying.

The glycol and polyhydric alcohol are most preferredly admixed after polymerization, and provide little or no benefit when added to water into which the interpolymer is to be dispersed. It is reasoned that the presence of the alcohol functionality will interfere or interact with the acid functionality of the acid polymer being formed. When added to the polymer post-polymerization, it is possible to control the conditions, such as excessive heat when drying, which could lead to interference or interaction.

The polyhydric alcohols are organic hygroscopic compositions, usually alcohols, which facilitate the wetting of the interpolymer particles in water. For the purpose of this disclosure, we mean the term "polyhydric alcohols" is to include all hygroscopic alcohol compositions including glycols, such as polyethylene glycol. The use of either a low surface tension surfactant or a polyhydric alcohol benefits the wetting of the polymer particles by aiding the wetting of the water by lowering the surface tension of the water and allowing it to penetrate the polymer particle or by drawing the particle to the water (or the water to the particle) via the hygroscopic mechanisms. As will be seen either benefits the wetting of the polymer without detriment to the use of the polymer as, e.g., a thickener.

The preferred polyhydric alcohols are glycerine (or glycerol). The preferred glycol is low molecular weight polyethylene glycol. Other polyhydric alcohols (or polyols) or glycols can be employed.

Examples of preferred linear block copolymeric steric stabilizers and random copolymeric comb steric stabilizers include fluorinated alkyl polyoxyethylene ethanols such as Fluorad FC-170C, fluorinated alkyl alkoxylate such as Fluorad FC-171, and ammonium perfluoroalkyl sulfonate such as Fluorad FC-120, all made by 3M.

The relative proportions of the steric stabilizer based upon the total weight of the olefinically unsaturated polymerizable carboxylic monomers and optional comonomers is generally from about 0.001 to about 20 percent, desirably from about 0.01 to about 10 percent, and preferably to about 0.2 to about 6.0 percent by weight.

The above crosslinked polymers, copolymers and interpolymers made from one or more olefinically unsaturated polymerizable carboxylic monomers are commercially available as Carbopol® 980 NF from BFGoodrich. Generally, other such crosslinked polymers, copolymers, etc., are available as various CARBOPOL® polymers from BFGoodrich, as various PEMULEN® polymers from BFGoodrich, as various NOVEON® polymers from BFGoodrich, as various HIVIS WAKO® polymers from Wako Junyaku Kogyo, and as various SYNTHALEN® polymers from 3 V Sigma.

It has been found that hydrogels capable of absorbing large amounts of water having unexpectedly low initial viscosities, and yet good tack and adhesion, as well as strong cohesion forces, which result in a rigid gel, are formed by blending the above crosslinked polymers, derived from olefinically unsaturated polymerizable carboxylic or anhydride monomers, with a high molecular weight substantially linear polymer derived from an olefinically unsaturated polymerizable carboxylic acid monomer. Such olefinic unsaturated acid monomers generally contain a carboxyl group and a total of from 3 to about 20 or 30 carbon atoms and preferably from 3 to about 7 carbon atoms. Specific examples include acrylic acid, methacrylic acid, maleic acid, itaconic acid, crotonic acid, citraconic acid, aconitic acid, fumaric acid, and the like. Preferred acids include acrylic and methacrylic, with acrylic acid being highly preferred. By the term "substantially linear" polymers which are derived from the olefinically unsaturated polymerizable carboxylic acids, it is meant that the polymer generally has 5 or less, desirably 3 or 2 or less, and preferably 1 or less side chains for every 100 repeat units of the polymer. Such polymers have a weight average molecular weight of generally from about 50,000 to about 2,000,000, desirably from about 200,000 to 1,000,000, and preferably from about 400,000 to about 600,000. Examples of suitable long chain high molecular weight polycarboxylic acids include CARBOPOL® 907, GOODRITE® K-702 and K-709 from BFGoodrich.

The polymeric blend is generally formed by dispersing a crosslinked polymer derived from olefinically unsaturated polymerizable carboxylic monomers into water. The amount of the polymer is generally from about 5 parts to about 30 parts by weight and desirably from about 10 parts to about 15 parts by weight for every 100 parts by weight of water. Similarly, the high molecular weight, linear polymer is dissolved in water in an amount of from about 5 to about 40 parts by weight and desirably from about 10 to about 20 parts by weight for every 100 parts by weight of water. The high molecular weight, linear polymer and the crosslinked polymer are then blended together. Optionally, additional water or other solvent such as alcohols, polyols, or polyalkoxides can be added. Such additional water or solvent is dependent upon the desired final qualities and physical constraints of individual formulations.

It has been found that the degree of neutralization of the hydrogel polymer blend has a direct impact on the ability of the blend to be non-covalently crosslinked; e.g., ionicly crosslinked or crosslinked by hydrogen bonding. Accordingly, the crosslinked polymer or copolymer and high molecular weight linear polyacid Is partially neutralized from an initial pH of from about 2.5 to about 3.5 to a pH of from about 3.5 to about 14, or about 10, or about 6.0, and desirably from about 4.2 to about 5.2. Neutralization can be carried out with any convenient neutralizing agent or compound such as ammonium hydroxide, sodium hydroxide, other alkali hydroxides, borates, phosphates, pyrophosphates or polyphosphates; AMP-95 (2-Amino-2-Methyl-1-Propanol) a product of Angus Chemical, cocamine, oleamine, diisopropanolamine, diisopropylamine, dodecylamine, Peg-15 cocoamine, morpholine, tetrakis(hydroxypropyl)ethylenediamine, triamylamine, triethanolamine, triethylamine, or tromethamine (2-Amino 2-Hydroxymethyl-1,3-propanediol). Preferred neutralizing agents include NaOH, tetrakis(hydroxypropyl)ethylenediamine, triethanolamine.

A viable non-covalent crosslinking system for the blend of a crosslinked polymer derived from olefinically unsaturated polymerizable carboxylic monomers and the high molecular weight linear polymer includes ionic crosslinkers such as polyvalent metal ions such as aluminum and zinc. The plus-3 oxidation state for aluminum is preferred and the plus-2 oxidation state for zinc is preferred. Desired compounds generally include halogen salts such as $AlCl_3$, $ZnCl_2$, $MgCl_2$, $CaCl_2$, $BCl_3$, $BF_3$, and the like. Sufficient amounts of the polyvalent metals are required to achieve crosslinking. Below a critical amount, the resulting hydrogel is too fluid. Above a critical amount, the metal ions are absorbed into the carboxyl forming an overly rigid, non-adhesive hydrogel The use of chemical crosslinks or the use of polymers already including chemical crosslinks in the form of microparticles or microgels can minimize the amount of ionic crosslinkers that are needed. This is desirable as the ionic crosslinkers may undesirably interact with many of the substances such as an active ingredient, decreasing the efficiency of delivery and sometimes preventing delivery. Reduction of the amount of ionic crosslinkers typically reduces any deleterious effect of the ionic crosslinkers. The amount of such ionic crosslinkers is dependent on the desired physical characteristics of the hydrogel and interactions with its various substances.

Other non-covalent crosslinking compounds include various crystallite crosslinked polymers such as polyvinyl alcohol, and the like.

Still other types of non-covalent crosslinking compounds include various hydrogen bonded compounds such as various complexes of polyacrylic acid with at least the following compounds: polyfunctional Lewis bases such as polyvinyl alcohol, polyvinyl pyrrollidone, polyethylene imine, polyethylene oxide, polypropylene oxide, glycosylated proteins, macromolecular polyols, polyacrylamide, and polysaccharides.

In order to prevent overly quick curing of the polymer blend and the formation of a rubber-like hydrogel, various cure rate modifiers are utilized such as monoalcohols, diols, and/or polyols such as glycerol. Examples of monoalcohols include methanol, ethanol, propanol, isopropanol, butanol, isobutanol, and t-butanol and monoethers of ethylene glycol, propylene glycol, polyethylene glycol, polypropylene glycol, and mixed ethylene oxide/propylene oxide glycols. Examples of diols include ethylene glycol, propylene glycol, butylene glycol, neopentyl glycol, ethoxy diglycol and hexylene glycol. Other suitable curing rate modifier agents include sugar solutions (xylitol, sorbitol), PEG (POE, polyoxyethylene, polyethylene glycol), PPG (polypropylene glycol), PEG/PPG (copolymers or blockpolymers), and the like. The amount of the alcohol utilized is generally from about 1 to about 80, desirably from about 10 to about 50, and preferably from about 20 to about 30 parts by weight for every part by weight of the ionic crosslinking agent.

The utilization of a cure rate modifier is to allow the hydrogel to be suitably shaped before cure occurs. For example, the hydrogel can be applied as a film to a backing such as nonwoven material, etc., as described herein above.

The hydrogel blends of the present invention are generally only partially swollen with respect to the full amount of water they can absorb. Such deficient amounts of water generally include from about 2 to about 10 and desirably from about 3 to about 5 times their original linear dimension. Otherwise, too much water results in too weak of a hydrogel, such that the adhesive force is stronger or greater than the cohesive force of the gel.

The hydrogel of the present invention can be utilized in various forms. One desired form is a so-called patch wherein the hydrogel containing the curing agent and the cure rate modifier, etc., is spread on a suitable backing. A release liner is then applied to the top of the hydrogel. The hydrogel is then allowed to cure. Another suitable form is a hydrogel in the form of a sheet or layer which contains a release layer on either side thereof or on both sides thereof. The hydrogel containing a substance therein be it a personal care compound, a pharmaceutical compound, an active ingredient, a biological active compound, an absorptive material, etc., can be wrapped in a suitable container such as an impervious plastic wrap, foil pouch, etc., and stored until needed. Then it can be applied to a desired substrate as noted herein below.

The applied substance can be any material known, purported, or thought to have beneficial effect on the chosen substrate such as the substances listed in the preceding paragraph. While water-soluble active ingredients are most easily incorporated, the use of nonwater carriers, emulsifiers, dispersed organic (hydrocarbon) phases, etc. can allow the delivery of nonpolar compounds (e.g. hydrocarbon materials such as aliphatic and aromatic compounds).

One class of substances are the therapeutic aids which include, but are not limited to, moisturizers (or things that help the substrate (skin) retain water); oils (or things that help the skin retain oil); antimicrobial agents; antibacterial agents; fungicide; anti-inflammatory/analgesic agents (e.g. things that reduce irritation); softening agents; toughening agents; agents that enhance elasticity of the substrate (e.g. skin); agents that enhance abrasion resistance of the substrate (e.g. skin, fabric, apparel), that provide some slipperiness to skin or fabric, or prevent pilling of fabric by other mechanisms; agents that otherwise change the texture of the substrate; agents that promote growth or cell reproduction; agents that retard growth or cell reproduction; stimulants for the cells or nerves; antihistamines; local anesthetics; etc.

The substance may remove unwanted components from the substrate such as removing oil, greases, irritants, nail polish, etc.; removing blemishes, defects, unusual texture, scars, growths (e.g. warts); removing hair; etc.

The hydrogel may apply an active ingredient with one or more of the following advantageous properties: sustained delivery, consistency in dosage, enhanced delivery, dosage control, efficiency, and bioavailability for: wound healing, burn healing, scar reducing, etc.; skin or keratin color changes (lightening, darkening, coloring), applying decorative images, highlighting; enhancing penetration of another active ingredient or medicine through the skin or other substrate; altering the fragrance or aroma of the substrate; reducing or enhancing fat, e.g. cellulite reduction; applying a hormone, steroid, or pheromone-, etc.

The active ingredient of the hydrogel may be of any polarity from low to high including fragrances, coloring, pigments, ointments, etc. Where desired, water solubility may be enhanced by the addition of other carriers, additives, etc. In many embodiments, a mixture of two or more active ingredients which act independently or in conjunction with each other will be used. The active ingredient can be any of the following: a moisturizer; an anti-aging agent (removing aging effect or repairing aging effects); an astringent; an acid (e.g. glycolic, citric, and vitamins); a skin stimulator (e.g. menthol, camphor, and cayenne pepper extract); a firming agent; a slimming agent; a radical scavenger; solubilizers; an antihistamine (e.g. diphenhydramine or chlorpheniramine maleate); methyl salicylate; glycol salicylate; an aromatherapeutic; a humectant; an emollient; a phytochemical (natural extract such as herbal and botanical e/.g. bamboo, tea tree oil, etc.); an antioxidant; a skin whitening agent (e.g. hydroquinone, peroxide, and kojic acid); a self tanning agent or agent for adding skin colorant (e.g. dihydroxy acetone); a skin protecting agent (e.g. moisturizers, waxes, sunblocks (organic or inorganic)); a spot remover (substrate may be people, clothing, animals, plants, hard surface, or fabric); keratin; retinol; vitamins; vitamin complexes; precursors of active ingredients such as precursors of retinol; salicylic acid and derivatives of salicylic acid; peptide; oligomeric and polymeric peptide; an enzyme; a coenzyme; proteins and their precursors; amino acid (e.g. dimers, cyclic and aliphatic amino acid); glycosamineoglycans; saccharides; derivatives of saccharides; polysaccharides, oligomeric saccharides; cyclic oligomeric saccharides; carbohydrates; fatty acid triglycerides, essential fatty acids; lipids; lecithin; phospholipids; conditioning agents; milk derivatives, carotenes; cyclodextrins; tocopherols; phytosterols; cationic agents; oil (natural such as animal and vegetable, synthetic including primrose oil, jojoba oil, mineral oil, castor oil, palm oil, coconut oil, corn oil, silicones, and derivatized forms thereof); gelatins, natural starch, modified starches, cellulosics and chemically modified cellulosics, sodium alginate, acacia, corn starch, casein, natural gums, and/or modified natural gums; waxes (natural such as plant and synthetic); quaternized compounds; silicone and/or silicone derivatives; protein hydrolyzates or derivatized proteins; chitin; denatured chitin; chitosan; marine derived compounds or marine origin materials (e.g. anything from the sea including things such as kelp, coral, seaweed, marine moisturizing factor, algae, sea plants, phytoplankton, kelp, and their extracts); hydrolyzed animal and/or vegetable protein; astringent (e.g. zinc oxide, tannic acid, alum, aluminum sulfate, vitamin, dl-$\alpha$-tocopherol); a wetting agent; a water repellent; an antimicrobial; a deodorant; a fungicide; a fruit acid; nut extracts/oils; a fragrance; flower acids; ceramides; a flavinoid; biologically derived materials (biotechnology); sodium hyaluronate; hyaluronic acid; etc.

It is also anticipated that the active ingredients can be added to the hydrogel after being blended with, contained within, and/or bound to another medium (liquid/solid or other). Examples include encapsulated ingredients, nanospheres, actives in zeolites, actives in oil, actives in liposomes, actives in glycospheres, etc.

The above substance added to the hydrogel be it a personal care compound, a pharmaceutical, an active ingredient, or the like, is generally added over a broad range of amounts depending upon the particular type of substance and the desired end result. The substance can be added to the blend of polymers prior to neutralization, or after neutralization but prior to ionic crosslinking or hydrogen bonding crosslinking. Alternatively, the substance can be added after the addition of the crosslinking agents but prior to the same curing. The crosslinking time will vary depending upon the amount of the various cure rate modifiers utilized and also upon the type of polymers utilized. As a rough rule of thumb, the desired cure time is approximately several hours to several days.

Substrates for application of the hydrogel compound include the skin, hair, and fingernails. The hair and fingernails can be grouped in the class of keratinous substrates. While personal use by humans is a preferred embodiment, uses on animals, plants, etc is not excluded. Hair substrates can be temporarily or permanently changed in color (including decorative images), texture (including adding or removing curls in hair), and for prevention of microbial, bacterial, and fungal activity on the substrate surface.

Substrates also include apparel, fabrics, hard surfaces, and vehicles including automobiles. For these substrates the improvements include but are not limited to sustained delivery (e.g. volatile components trapped in the hydrogel do not evaporate as quickly as when applied directly to the substrate and are available to the substrate over the entire treatment period), consistency in dosage, enhanced delivery, controlled dosage amount, efficiency, etc. A preferred embodiment for these substrates is those applications or active ingredients, which are adversely affected by atmospheric oxygen. The exposure of the substrate surface to atmospheric oxygen is restricted during the time the cataplasm is in place and this allows more effective use of oxygen sensitive compounds. Depending on the particular substrate and cataplasms for these substrates, the stability at various storage and use temperatures can vary widely.

The physical integrity of the hydrogel is desirably such that fracture and/or fragmentation of the hydrogel does not occur during storage and use. If the hydrogel is adhesive or has an adhesive layer attached thereto to better secure its relative location on the substrate during delivery or removal of the active ingredient(s), then the hydrogel desirably has a cohesive strength in excess of the adhesion value to the substrate.

The hydrogel, in addition to the substance, can contain various conventional additives in any desired amount. Such additives include clay, herb and herbal extracts, chemical compounds and materials which absorb undesirable components from skin or other substrates, adsorption enhancers, desorption enhancers, absorption enhancers, humectants (e.g. glycerin, propylene glycol, sorbitol), water miscible or immiscible organic solvents (or other active carriers or active reservoirs), adhesive and/or a polymer that imparts adhesivity to the hydrogel (e.g. polyvinyl alcohol)—may be important to adhere cataplasm to backing or adhere cataplasm to substrate—, gel support media or polymer to interconnect hydrogel particles, modulus modifier, tensile strength modifier, elongation to break modifier—these conform the hydrogel and cataplasm physical properties to the application requirements—, gelation rate regulator (e.g. EDTA, citric acid, lactic acid, tartaric acid, and polyacrylic acid, also called chelating agents), additives to reduce negative interaction by hydrogel to substrate (irritation, inflammation or corrosion)—may be as simple as pH adjuster, oil, wax, etc—, etc.

A preferred form of application of the hydrogel is in the form of a patch wherein the hydrogel is located on a backing and the hydrogel optionally has a release liner thereon. The backing can be made of any suitable natural or synthetic fiber or fabric, and can be woven or non-woven. Examples of fibers or natural fabrics include cotton, wool and the like. Examples of synthetic fibers or fabrics include polyester such as polyethyleneterephthalate, polyethylene, polypropylene, nylon, acetate and the like. The backing can also be in the form of an impermeable or permeable foam made from natural materials or from synthetic materials such as polyolefin, polyester, polyurethane, and the like. Thickness of the backing can vary widely as from 1, 3 or 5 to about 10, 20, 30, 40, and even 50 mils. The release liner can be a plastic such as a polyolefin, for example polyethylene or polypropylene, or it can be polyvinylchloride, nylon, and the like. Optionally, it can contain a release liner thereon such as a thin layer of silicone. The patch can be applied to a substrate such as human skin simply by removing the release liner and applying the hydrogel, containing the backing thereon, thereto.

The present invention will be better understood by reference to the following examples which serve to illustrate, but not to limit the present invention.

Formulations
Oil/Water Hydrogel Formulation

| Phase | Ingredient | % (w/w) | Function |
|---|---|---|---|
| A | Carbopol ® 980 NF (11.25% aq) | 40.00 | crosslinked polymer |
|  | Carbopol ® 907 (20.00% aq) | 17.50 | linear polymer |
|  | DI Water | 10.36 | dilluent/solvent |
|  | Methyl Salicylate | 11.00 | substance:active ingredient |
| B | Menthol | 7.70 | substance:active ingredient |
|  | Camphor | 3.30 | substance:active ingredient |
| C | NaOH(18% aq) | 4.00 | Neutralizer |
|  | $AlCl_3 \cdot 6H_2O$ | 0.14 | ionic crosslinker |
| D | Glycerin | 5.00 | cure rate modifier |
|  | DI Water | 1.00 | dilluent/solvent |

Procedure:

1. A was combined in a Hobart mixer and blended at low speed until smooth (~10 min).

2. B was combined and mixed in a sealed vessel until the menthol and camphor were dissolved.

3. B was added to Phase A and blended at low speed in the Hobart mixer until homogeneous (~15 min).

4. C is added to Phases A+B and mixed at medium speed in the Hobart mixer until a smooth emulsion/suspension was observed (~15 min).

5. D was combined with mixing until all of the $AlCl_3.6H_2O$ was solubilized.

6. D was added to Phases A+B+C and mixed at medium speed in the Hobart mixer until homogeneous (~15 min).

7. A portion of the finished formulation was drawn onto a fabric backing and topped with a release liner to form a "patch".

These formualtions relate to a range of properties:

| Formulation | Carbopol ® 980 NF | Carbopol ® 907 | Dl Water | Glycerin | AlCl3 | NaOH (18%) | Peak Force of Adhesion | Energy of Adhesion |
|---|---|---|---|---|---|---|---|---|
| 1 | 3.00 | 2.00 | 87.42 | 5.00 | 0.08 | 2.50 | 8.70 | 14.29 |
| 2 | 3.00 | 3.00 | 80.84 | 10.00 | 0.16 | 3.00 | 9.80 | 11.90 |
| 3 | 3.00 | 4.00 | 81.88 | 7.50 | 0.12 | 3.50 | 13.00 | 67.69 |
| 4 | 4.00 | 2.00 | 80.88 | 10.00 | 0.12 | 3.00 | 9.80 | 19.72 |
| 5 | 4.00 | 3.00 | 81.92 | 7.50 | 0.08 | 3.50 | 11.40 | 59.18 |
| 6 | 4.00 | 4.00 | 82.84 | 5.00 | 0.16 | 4.00 | 16.40 | 17.44 |

-continued

These formualtions relate to a range of properties:

| Formulation | Carbopol ® 980 NF | Carbopol ® 907 | Dl Water | Glycerin | AlCl3 | NaOH (18%) | Peak Force of Adhesion | Energy of Adhesion |
|---|---|---|---|---|---|---|---|---|
| 7 | 5.00 | 2.00 | 81.84 | 7.50 | 0.16 | 3.50 | 9.10 | 7.68 |
| 8 | 5.00 | 3.00 | 82.88 | 5.00 | 0.12 | 4.00 | 12.00 | 17.91 |

As apparent from the above tables, the formulations of the present invention utilizing the blend of at least one crosslinked polymer derived from at least one olefinically unsaturated carboxylic monomer and at least one high molecular weight linear polymer derived from at least one olefinically unsaturated carboxylic acid monomer form suitable hydrogels exhibiting a controllable range of physical attributes as noted by the peak force of adhesion as well as the energy of adhesion values.

While in accordance with the Patent Statutes the best mode and preferred embodiment have been set forth, the scope of the invention is not limited thereto but rather by the scope of the claims.

What is claimed is:

1. An aqueous polymeric composition, comprising:
a blend of at least one crosslinked polymer and at least one high molecular weight substantially linear carboxylic acid-based polymer.
said crosslinked polymer derived from
(a) a polymer made from at least one olefinically unsaturated carboxylic acid or anhydride monomer, or
(b) a copolymer of said at least one olefinically unsaturated carboxylic acid or anhydride monomer and a comonomer, or
(c) an interpolymer of said (a) or said (b), or combinations thereof,
with the proviso that when said crosslinked polymer is said (b) copolymer or said (c) interpolymer of said (b), the amount of comonomer forming said copolymer is from about 0.001 to about 30 percent by weight of said copolymer; and
said at least one high molecular weight substantially linear carboxylic acid-based polymer derived from at least one olefinically unsaturated carboxylic acid monomer, said crosslinked polymer being crosslinked by a crosslinking agent, and said high molecular weight substantially linear carboxylic acid-based polymer having a weight average molecular weight of at least 200,000.

2. An aqueous polymeric composition according to claim 1,
wherein said at least one olefinically unsaturated carboxylic acid or anhydride monomer has a total of from 3 to about 34 carbon atoms,
wherein said (b) copolymer is derived from said at least one olefinically unsaturated carboxylic acid or anhydride monomer having a total of from 3 to about 34 carbon atoms with a comonomer of acrylic ester, acrylamide, olefin, vinyl ester, vinyl ether, vinyl amide, amine, or styrenic monomer, or combinations thereof having a total of from 3 to about 40 carbon atoms; and
wherein said (c) interpolymer is derived from the preparation of said (a), or said (b), in the presence of a steric stabilizer surfactant having at least one hydrophilic moiety and at least one hydrophobic moiety in a linear block or a random comb configuration, and wherein the amount of said steric stabilizer is from about 0.001 to about 20 percent by weight based upon the weight of said (a) polymer or said (b) copolymer.

3. An aqueous polymeric composition according to claim 2, wherein said high molecular weight substantially linear polymer has 5 side chains or less per 100 repeat units.

4. An aqueous polymeric composition according to claim 3, wherein said at least one olefinically unsaturated carboxylic acid monomer utilized to form said high molecular weight substantially linear polymer has a total of from 3 to 30 carbon atoms, wherein said high molecular weight substantially linear polymer has 3 side chains or less per 100 repeat units, and wherein said high molecular weight substantially linear polymer has a weight average molecular weight of from about 200,000 to about 2,000,000.

5. An aqueous polymeric composition according to claim 4, wherein the amount of said crosslinked polymer is from about 2.5 parts to about 15 parts by weight and wherein the amount of said high molecular weight substantially linear polymer is from about 2.5 to about 20 parts by weight per 100 parts by weight of water.

6. An aqueous polymeric composition according to claim 5, wherein said interpolymer is formed from an aqueous solution containing a low surface tension surface active agent which is a hydrocarbon, a fluorocarbon, or a silicone surface active agent.

7. An aqueous polymeric composition according to claim 5, wherein said (a) monomer is acrylic acid, methacrylic acid, maleic acid, or maleic anhydride monomer, or combinations thereof, and wherein said high molecular weight substantially linear polymer is derived from a monomer comprising acrylic acid, methacrylic acid, or combinations thereof.

8. An aqueous polymeric composition according to claim 7, wherein said crosslinking agent forming said at least one crosslinked polymer is allyl pentaerythritol, trimethylolpropane dialylether, allyl sucrose, or combinations thereof, and wherein said high molecular weight substantially linear polymer has a molecular weight of from about 200,000 to about 1,000,000, wherein said comonomer is present in an amount from about 0.01 to about 20 percent by weight of said copolymer, and wherein the amount of said steric stabilizer is from about 0.01 to about 10 percent by weight.

9. An aqueous polymeric composition according to claim 7, including a ionic crosslinking agent.

10. An aqueous polymeric composition according to claim 1, including an non-covalent crosslinking agent.

11. An aqueous polymeric gel composition comprising: an aqueous blend of:
at least one crosslinked polymer and at least one high molecular weight substantially linear carboxylic acid-based polymer,
said crosslinked polymer derived from
(a) a polymer made from at least one olefinically unsaturated carboxylic acid or anhydride monomer, or (b) a copolymer of said at least one olefinically unsaturated carboxylic acid or anhydride monomer and a comonomer, or (c) an interpolymer of said (a) or said (b), or combinations thereof, with the proviso that when said crosslinked polymer is said (b) copolymer or said (c) interpolymer of said (b), the amount of comonomer forming said copolymer is from about 0.001 to about 30 percent by weight of said copolymer; and said at least one high molecular weight substantially linear carboxylic acid-based polymer derived from at least one olefinically unsaturated carboxylic acid monomer, said crosslinked polymer being crosslinked by a crosslinking agent, and said high molecular weight substantially linear carboxylic acid-based polymer having a weight average molecular weight from about 200,000 to about 2,000,000.

12. An aqueous polymeric gel composition according to claim 11, wherein said at least one olefinically unsaturated carboxylic acid or anhydride monomer has a total of from 3 to about 34 carbon atoms, wherein said (b) copolymer is derived from said at least one olefinically unsaturated carboxylic acid or anhydride monomer having a total of from 3 to about 34 carbon atoms with a comonomer of acrylic ester, acrylamide, olefin, vinyl ester, vinyl ether, vinyl amide, amine, or styrenic monomer, or combinations thereof having a total of from 3 to about 40 carbon atoms; and wherein said (c) interpolymer is derived from said (a), or said (b) in the presence of a steric stabilizer surfactant having at least one hydrophilic moiety and at least one hydrophobic moiety in a linear block or a random comb configuration, and wherein the amount of said steric stabilizer is from about 0.001 to about 20 percent by weight based upon the weight of said (a) polymer or said (b) copolymer.

13. An aqueous polymeric gel composition according to claim 12, wherein said high molecular weight substantially linear polymer has 5 side chains or less per 100 repeat units, and wherein the weight average molecular weight of said substantially linear polymer is from about 200,000 to about 1,000,000.

14. An aqueous polymeric gel composition according to claim 13, wherein said at least one olefinically unsaturated carboxylic acid monomer utilized to form said high molecular weight substantially linear polymer has a total of from 3 to 30 carbon atoms, and wherein said high molecular weight substantially linear polymer has 3 side chains or less per 100 repeat units.

15. An aqueous polymeric gel composition according to claim 14, wherein the amount of said crosslinked polymer is from about 2.5 parts to about 15 parts by weight and the amount of said high molecular weight substantially linear polymer is from about 2.5 to about 20 parts by weight per 100 parts by weight of water.

16. An aqueous polymeric gel composition according to claim 15, wherein said interpolymer is formed from an aqueous solution containing a low surface tension surface active agent which is a hydrocarbon, a fluorocarbon, or a silicone surface active agent.

17. An aqueous polymeric gel composition according to claim 15, wherein said (a) monomer is acrylic acid, methacrylic acid, maleic acid, or maleic anhydride monomer, or combinations thereof, and wherein said high molecular weight substantially linear polymer is derived from a monomer comprising acrylic acid, methacrylic acid, or combinations thereof.

18. An aqueous polymeric gel composition according to claim 17, wherein said crosslinking agent forming said at least one crosslinked polymer is allyl pentaerythritol, trimethylolpropane dialylether, allyl sucrose, or combinations thereof, and wherein said high molecular weight substantially linear polymer has a molecular weight of from about 200,000 to about 1,000,000, wherein said comonomer is present in an amount from about 0.01 to about 20 percent by weight of said copolymer, and wherein the amount of said steric stabilizer is from about 0.01 to about 10 percent by weight.

19. An aqueous polymeric gel according to claim 17, including an ionic crosslinking agent.

20. An aqueous polymeric gel composition according to claim 11, including a non-covalent crosslinking agent.

* * * * *